US006669697B1

(12) United States Patent
Pisharodi

(10) Patent No.: US 6,669,697 B1
(45) Date of Patent: Dec. 30, 2003

(54) SELF-RETAINING BOLT FOR INTERNAL SPINAL STABILIZERS

(75) Inventor: Madhavan Pisharodi, Brownsville, TX (US)

(73) Assignee: Perumala Corporation, Brownsville, TX (US)

( * ) Notice: Subject to any disclaimer, the term of this patent is extended or adjusted under 35 U.S.C. 154(b) by 169 days.

(21) Appl. No.: 09/641,448

(22) Filed: Aug. 17, 2000

Related U.S. Application Data

(63) Continuation-in-part of application No. PCT/US99/22232, filed on Sep. 24, 1999, and a continuation-in-part of application No. 09/161,141, filed on Sep. 25, 1998, now Pat. No. 6,355,038.

(51) Int. Cl.⁷ .............................................. A61B 17/56
(52) U.S. Cl. ...................................................... 606/61
(58) Field of Search ............................. 606/61, 60, 70, 606/71; 403/61, 408.1

(56) References Cited

U.S. PATENT DOCUMENTS

| 3,731,961 | A | * | 5/1973 | Becker .......................... 403/61 |
| 4,696,290 | A | | 9/1987 | Steffee |
| 5,047,029 | A | | 9/1991 | Aebi et al. |
| 5,084,049 | A | * | 1/1992 | Asher et al. ................... 606/61 |
| 5,092,866 | A | | 3/1992 | Breard et al. |
| 5,092,893 | A | * | 3/1992 | Smith .......................... 606/61 |
| 5,129,899 | A | | 7/1992 | Small et al. |
| 5,171,279 | A | | 12/1992 | Mathews |
| 5,201,734 | A | | 4/1993 | Cozad et al. |
| 5,312,404 | A | | 5/1994 | Asher et al. |
| 5,344,421 | A | | 9/1994 | Crook |
| 5,531,747 | A | * | 7/1996 | Ray ............................. 606/61 |
| 5,683,391 | A | | 11/1997 | Boyd |
| 5,707,372 | A | * | 1/1998 | Errico et al. .................. 606/61 |
| 5,716,357 | A | | 2/1998 | Rogozinski |
| 5,743,907 | A | | 4/1998 | Asher et al. |
| 5,906,466 | A | | 5/1999 | Eandi |
| 6,355,038 | B1 | | 3/2002 | Pisharodi |

FOREIGN PATENT DOCUMENTS

| EP | 0846444 | 6/1998 |
| FR | 2683445 | 5/1993 |
| FR | 2697993 | 5/1994 |
| FR | 2735011 | 12/1996 |
| GB | 1243353 | 8/1971 |
| WO | WO 0018312 | 4/2000 |

OTHER PUBLICATIONS

Smith & Nephew Spine brochure, Simmons Palting System–Kambin Offset Bolt (Smith & Nephew Spine, a Division of Smith & Nephew Richards Inc., Memphis TN) Date unknown.*

(List continued on next page.)

Primary Examiner—Todd E. Manahan
(74) Attorney, Agent, or Firm—Mark R. Wisner

(57) ABSTRACT

A multi-axis correction washer for use with a spinal stabilizer for internal spinal fixation. The body of the washer is provided in cylindrical and wedge-shaped cylindrical configurations with a passage through the center axis of the longitudinal axis of the cylinder and/or offset from the center axis of the cylindrical washer and a shoulder or other structure for rotatably engaging an aperture in a spinal implant. The spinal implant can be a plate and screw-type, ladder-type, or monorail-type spinal fixation system. The washer is provided with a concave surface and a bearing surface, the former being adapted to engage the hemispherically-shaped head of the pedicle screw and the nut threaded onto the pedicle screw bearing against the latter. The washer is rotated to provide an infinite range of angles and pedicle screw placements relative to the central axis of the spinal column for maximum flexibility of installation and to effectively transfer the load on the spinal column to the implant, all while maintaining an angle of approximately 90° between the head of the screw and/or nut and the washer that engages the implant.

8 Claims, 11 Drawing Sheets

OTHER PUBLICATIONS

Moss Miami Titanium brochure (Depuy otech, Warsaw IN 1996).*

Dynalok Anterior Fixation System borchure (Danek Medical Inc. Mephis TN, Apr. 1993).*

Brantigan, J.W., et al., Posterior Lumbar Interbody Fusion Technique Using the Variable Screw Placement Spinal Fixation System, in D.M. Arnold, et al. (Eds.), Spine: Pedicle Fixation of the Lumbar Spine, Hanley & Belfus, Inc., Philadelphia, pp. 175–200 (1992).

Heim, S.E., et al., Danek Plate and Screw System, in D.M. Arnold, et al. (Eds.), Spine: Pedicle Fixation of the Lumbar Spine, Hanley & Belfus, Inc., Philadelphia, pp. 210–234 (1992).

Edwards, C.C., The Edwards Modular System for Three–Dimensional Control of Lumbar Spine, in D.M. Arnold, et al. (Eds.), Spine: Pedicle Fixation of the Lumbar Spine, Hanley & Belfus, Inc., Philadelphia, pp. 235–263 (1992).

An, H.S. and J.M. Cotler (eds.), Spinal Instrumentation, Williams & Wilkins, Baltimore, MD, pp. 197–217, 399–400, 435–456 (1992).

Kostuik, J.P., Anterior Kostuik–Harrington Distraction Systems for the Treatment of Acute and Chronic Kyphotic Deformities, in R.G. Fessler and R.W. Haid, Eds., Current Techniques in Spinal Stabilization, pp. 171–192 (1996).

Fessler, R.G., et al., Utilization of the Texas Scottish Rite Hospital Universal System for Stabilization of the Thoracic and Lumbar Spine, in R.G. Fessler and R.W. Haid, Eds., Current Techniques in Spinal Stabilization, pp. 273–285 (1996).

Gillet, P., Utilization of the Compact Cotrel–Dubousset System for Stabilization of the Thoracolumbar and Lumbar Spine, in R.G. Fessler and R.W. Haid, Eds., Current Techniques in Spinal Stabilization, pp. 297–308 (1996).

Simmons, J.W., Utilization of the Simmons Plating System for Stabilization of the Spine, in R.G. Fessler and R.W. Haid, Eds., Current Techniques in Spinal Stabilization, pp. 325–332 (1996).

Rengachary, S.S., et al. Segmental Fixation of the Lumbosacral Spine Using the Isola/VSP System, in R.G. Fessler and R.W. Haid, Eds., Current Techniques in Spinal Stabilization, pp. 367–378 (1996).

Versalok Low Back Fixation System brochure (Wright Medical Technology, Arlington, TN, 1996).

Simmons Plating System Catalog, Surgical Technique (Smith & Nephew Spine, a Division of Smith & Nephew Richards Inc., Memphis, TN, Oct. 1993).

Rogozinski, C., et al., The Rogozinski Spinal Rod System: A New Internal Fixation of the Spine, in D.M. Arnold, et al. (Eds.), Spine: Pedicle Fixation of the Lumbar Spine, Hanley & Belfus, Inc., Philadelphia, pp. 107–120 (1992).

Krag, M.H., Vermont Spinal Fixator, in D.M. Arnold, et al. (Eds.), Spine: Pedicle Fixation of the Lumbar Spine, Hanley & Belfus, Inc., Philadelphia, pp. 120–145 (1992).

* cited by examiner

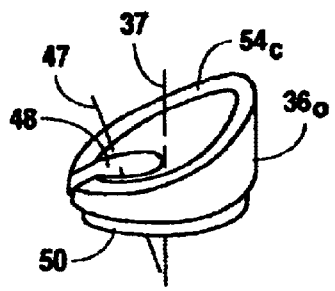
FIG. 10A
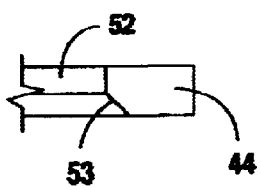
FIG. 13
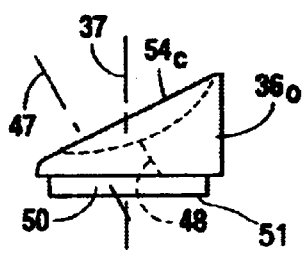
FIG. 10B
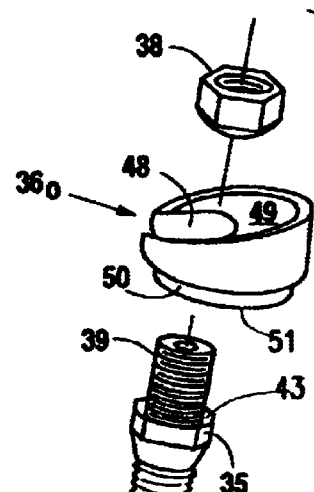
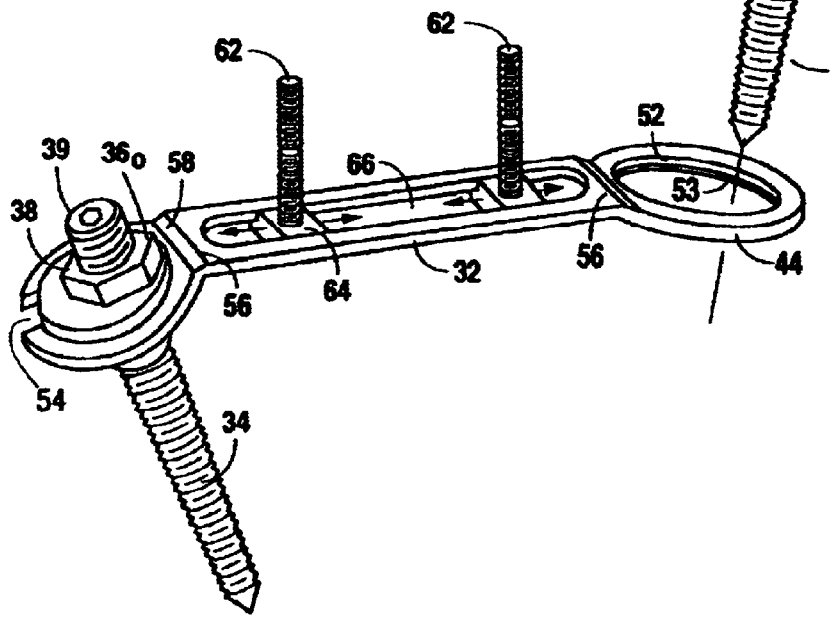
FIG. 12

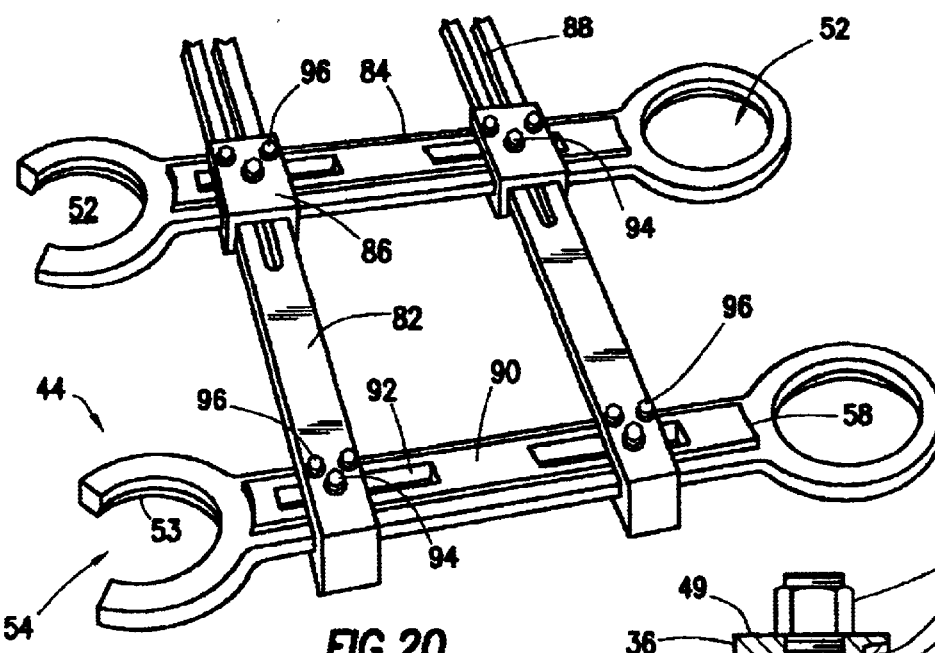
FIG.20
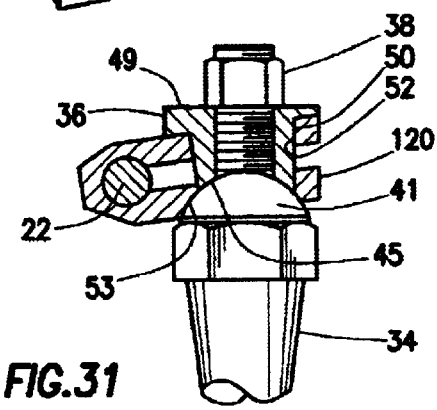
FIG.31
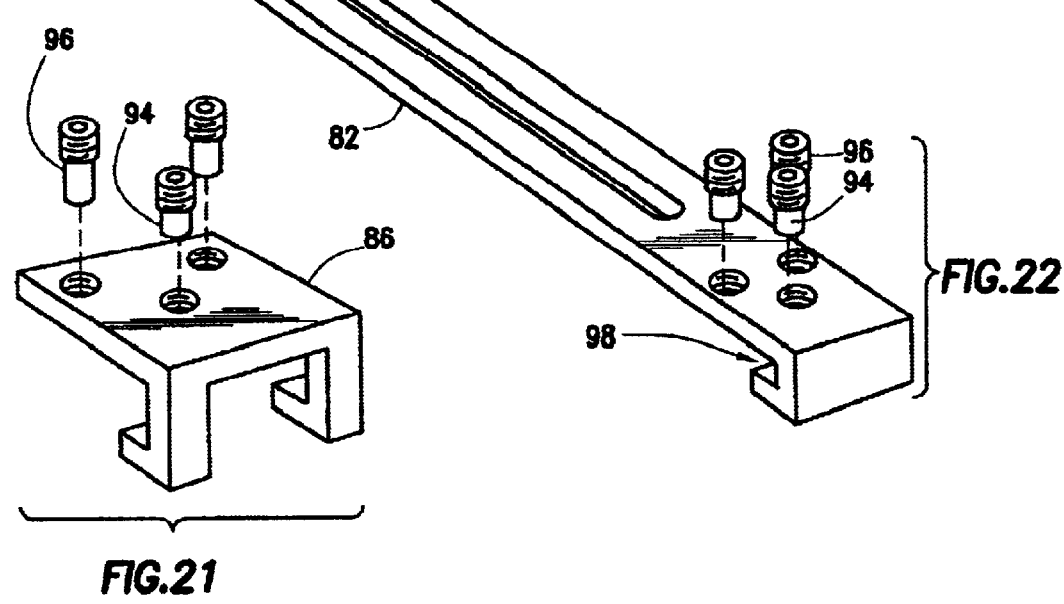
FIG.21
FIG.22

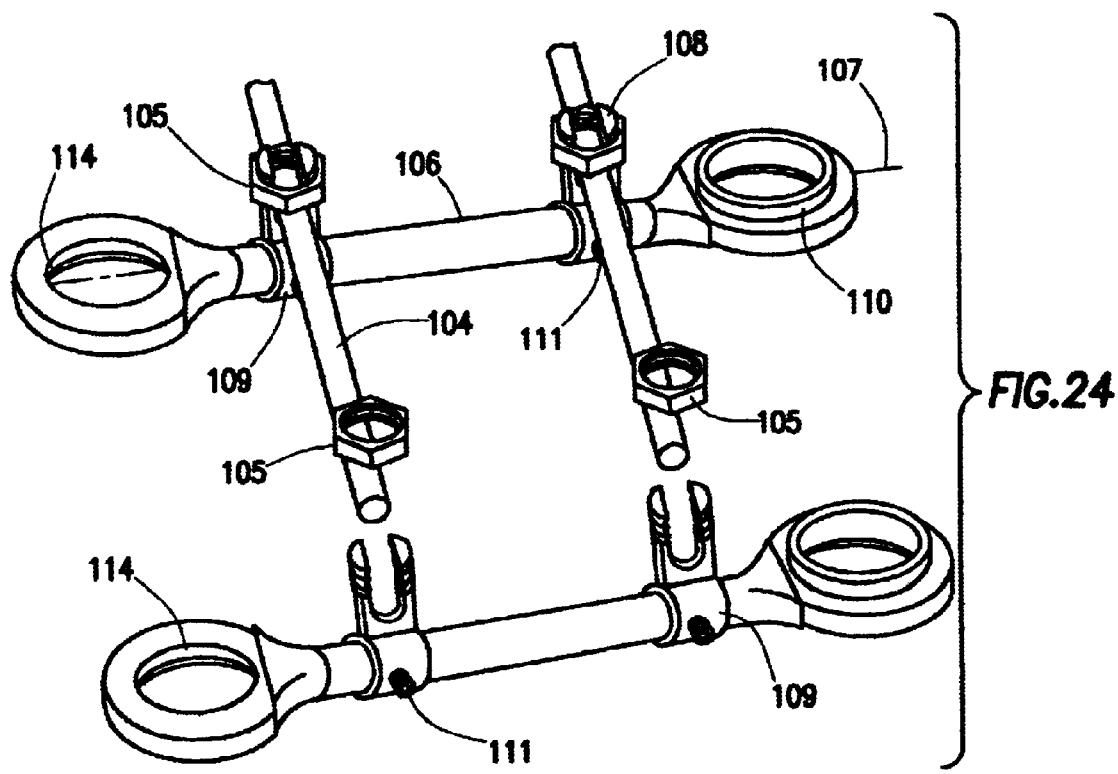
*FIG.24*
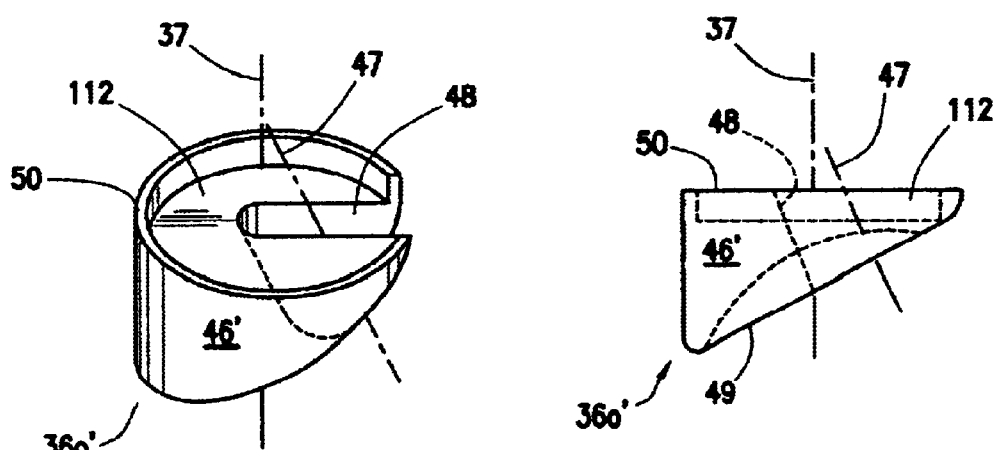
*FIG.25*     *FIG.26*

SELF-RETAINING BOLT FOR INTERNAL SPINAL STABILIZERS

This application is a continuation-in-part of International Application No, PCT/US99/22232, filed Sep. 24, 1999 and entitled MULTI-AXIS APPARATUS AND METHODS FOR TRANSFERRING LOAD FROM SPINAL COLUMN TO INTERNAL SPINAL STABILIZERS. International Application No. PCT/US99/22232 was filed as a continuation-in-part of application Ser. No. 09/161,141, filed Sep. 25, 1998, now U.S. Pat. No. 63,355,038 entitled MULTI-AXIS INTERNAL SPINAL FIXATION, and this application is also, being filed as a continuation-in-part of application Ser. No. 09/161141 now U.S. Pat. No. 6,355, 038.

The present invention relates to apparatus and methods of multi-axis internal spinal fixation. In more detail, the present invention relates to a connection for use in an internal spinal fixation system, and a method of stabilizing, or fixing, the spine for use with either bilateral rods or plates (such as the Steffee/variable screw placement (VSP) system) or a central rod and plurality of cross-bars or plates (such as the so-called Tacoma Monorail System), utilizing wedge-shaped and/or flat washers having concave surfaces and, optionally, off-set and/or centered openings therein to provide multiple axes for transfering load from the patient's spinal column to the stabilizer through the pedicle screws used to fix the rods, cross-bars, and/or plates to the vertebrae of the patient.

There are many systems available for internal fixation of the spine. Such systems are described in the patent literature (see, for instance, U.S. Pat. Nos. 4,696,290, 5,047,029, 5,092,866, 5,129,899, 5,201,734, 5,312,404, 5,531,747, and 5,743,907 and European Application No. EP 0 846 444 A1) and the scientific literature (see, for instance, D. M. Arnold and J. E. Lonstein (Eds.), 6 State of the Art Reviews—Spine: Pedicle Fixation of the Lumbar Spine (Philadelphia: Nanley & Belfus, Inc.) 1992 and H. S. An and J. M. Cotler (Eds.), Spinal Instrumentation (Baltimore: Williams & Wilkins) 1992), and are available from such vendors as AcroMed, Smith & Nephew, MOSS® Miami, Osteonics, Sofamor Danek, and others.

A problem with all such systems, however, is the connection between the screws used to affix the system to the pedicle and the rods, cross-bars, and/or plates of the system. As stated in J. M. Cotler, et al., Principles, Indications, and Complications of Spinal Instrumentation: A Summary Chapter, in H. S. An and J. M. Cotler, Spinal Instrumentation pp. 435–456 (Baltimore: Wiliams & Wilkins) 1992, "[a] significant problem in pedicular screw fixation appears to be at the site of linkage between the screw and rod or plate."

It appears that the problems at the site of this linkage may result from the geometry of the connection between the screw and the rod or plate. This difficult geometry results from several factors, including the different angles of the pedicles of the vertebrae, the location of the vertebrae and their relative sizes, the shape of the vertebrae and the spacing between vertebrae, the placement of the screws, the lordosis of the spine, and the need to insert the screws into each vertebra at an angle. With regard to the angle of the pedicle screws, pedicle screws are angled inwardly and upwardly into the vertebra for maximum strength and, because the surfaces of the pedicles of each vertebrae are angled relative to each other, the screws rarely line up across the vertebral body into which they are screwed. Nor do they usually line up from one vertebra to the adjacent vertebra, even if the adjacent vertebrae are the same size and shape (which they generally are not). For a more complete, discussion of the biomechanics of the bone-implant interface, reference is made to H. A. pool and R. W. Gaines, Biomechanics of Transpedicular Screw Spinal Implant Systems, in D. M. Arnold and J. E. Lonstein (Eds.), 6 State of the Art Reviews—Spine: Pedicle Fixation of the Lumbar Spine 37–44 (Philadelphia: Nanley & Belfus, Inc.) 1992, M. R. Pinto, Complication of Pedicle Screw Fixation, in D. M. Arnold and J. E. Lonstein (Eds.), 6 State of the Art Reviews—Spine: Pedicle Fixation of the Lumbar Spine 45–54 (Philadelphia: Nanley & Belfus, Inc.) 1992, and M. H. Krag, Vermont Spinal Fixator, in D. M. Arnold and J. E. Lonstein (Eds.), 6 State of the Art Reviews—Spine: Pedicle Fixation of the Lumbar Spine 121–145 (Philadelphia: Nanley & Belfus, Inc.) 1992, which references are incorporated herein in their entirety by these specific references thereto. A rod (or rods depending upon the particular stabilizer utilized) running along the longitudinal axis of the patient's spinal column provides the structural rigidity required for the stabilizer to stabilize the spine. Because the pedicle screws do not line up, the rod(s) must either be bent to the location of each screw head or structure must he provided that can be adjusted and/or positioned to enable the head of the pedicle screw to contact the rod(s) to transfer load from he screw to the rod.

As a result of this difficulty, the literature includes comments such as the following tatement in R. M. Puno and J. A. Byrd III, Transpedicular Screw/Rod Fixation Using the Puno-Winter-Byrd (PWB) System, in D. M. Arnold and J. E. Lonstein (Eds.), 6 State of the Art Reviews—Spine: Pedicle Fixation of the Lumbar Spine 83–106 (Philadelphia: Nanley & Belfus, Inc.) 1992:

"Transpedicular fixation has been proved to be of value in the treatment of spinal disorders . . . However, experience has shown that this method of instrumentation places great demand on the surgeon's skill because of the anatomic constraints related mainly to the anatomy and morphometry of the spinal pedicle."

Many of the above-listed systems, and many of the systems described in the literature, attempt to relieve this burden on the surgeon by providing angled screws (for instance, the AMSET® R-F reduction-fixation system), so-called polyaxial screws (available from MOSS® Miami), full-length, scalloped, open-slot plate designs with an under-surface complementary to the shape of the screw head for positioning of the screws and up to 15° medial-lateral and 30° craniocaudal angulation at the screw-plate interface, and infinitely variable couplers (the so-called Rogozinski spinal rod system, for exanple) that are said to allow rotation through a 130° arc to allow screw placement within the pedicle without requiring that each screw be aligned with the screw in the adjacent vertebrae.

Although they address these problems, as evidenced by the introduction of new systems by the same vendors marketing the above-listed systems, no system completely solves all the problems presented by the need for optimal screw placement, angulation of the screw, and effective load transfer from spinal column to stabilizer. An ideal system would (a) accomodate optimal screw placement, height, and angulation, (b) accomodate different sizes and shapes of vertebrae, (c) minimize (or not require) bending or other fabrication during surgery, (d) maintain an angle of approximately 90° at the connection between the screw head and the plate or cross-bar to which the screw is attached for optimal load transfer and to minimize the likelihood of slippage and/or gross failure, and (e) be strong enough to provide lasting and rigid fixation of the spine. Those skilled in the art will recognize that this list is not exhaustive, but instead illustrates some of the characteristics of an ideal internal fixation system. Other design criteria are also important, and some practicioners may consider some criteria so important that they might not even list others.

So far as is known, none of the above-listed internal fixation systems meets these criteria in every patient. The disadvantages and limitations of currently available systems are made clear from reports in the literature of failure rates (failure of the device, not such complications as infection, phlebitis, seroma, neurologic deficit, etc.) as high as 25% (see R. Roy-Camille, et al., 203 Clin. Orthop. 7 (1986)), 11% (see, S. F. Heim and E. R. Luque, Danek Plaste and Screw System, in D. M. Arnold and J. E. Lonstein (Eds.), 6 State of the Art Reviews—Spine: Pedicle Fixation of the Lumbar Spine 201–234 (Philadelphia: Nanley & Belfus, Inc.) 1992), 8% (see, R. M. Puno and J. A. Byrd III, Transpedicular Screw/Rod Fixation Using the Puno/Winter/Byrd (PWB) System, supra), and 2–7% D. M. Arnold and L. L. Wiltse, The Wiltse System of Internal Fixation for the Lumbar Spine, in D. M. Arnold and J. E. Lonstein (Eds.), 6 State of the Art Reviews—Spine: Pedicle Fixation of the Lumbar Spine 55–82 (Philadelphia: Nanley & Belfus, Inc.) 1992).

The currently available systems have other limitations. By way of example, so far as is known, no currently available surgically implanted system can predictably treat rotoscoliosis. Further, no currently available system is conveniently used in multiple level surgery. Multiple level surgery is a challenge for the surgeon because of the need to align the pedicle screws in multiple vertebrae while working under the heavy muscles of the back.

There is therefore a need for improvement of such systems, and it is this improvement to which the present invention is directed. In particular, it is an object of the present invention to improve the screw-plate interface in those systems in which the screw is angled and/or spaced at varying intervals. Another object of the present invention is to provide flexibility of placement, angulation, spacing, and screw height for accomodating the pedicle screws of such systems. Another object of the present invention is to provide a load transfer system that is universal in the sense that, although comprised of relatively few parts, it works with pedicle screws and laminar hooks, thereby providing even more flexibility and ease of use. Another object of the present invention is to provide an internal spinal fixation system that avoids the need for surgery under the heavy muscles of the back so that implantation is simplified and there is more room for fusion of adjacent vertebrae in the lateral gutter. Other objects, and the advantages, of the present invention will be made clear to those skilled in the art by the following description of the preferred embodiments thereof These, and other objects, of the present invention to be made clear by the following detailed description of the invention, are met by providing a connection between a spinal stabilizer and a pedicle screw with a hemispherical head comprising a washer defining means for engaging a spinal stabilizer, means on the spinal stabilizer for engaging the washer, the engaging means on the washer and the engaging means of the spinal stabilizer cooperating to engage each other at a plurality of points within a common plane. The washer defines a concave surface, a bearing surface, and a passage extending through the washer for receiving the pedicle screw therethrough with the hemispherical head bearing against the concave surface of the washer when a nut bears against the bearing surface when the spinal stabilizer is affixed to a vertebral body. In one embodiment, the engaging means on the washer comprises means for resting on and rotatably engaging in the spinal stabilizer adjacent the periphery of an aperture in the spinal stabilizer so that the washer is capable of being rotated in the aperture, the combination of the concave surface and the different angles and positions of the screw providing an infinite variety of angles and pedicle screw placements while maintaining an optimal interface between the head of the screw and the washer so as to effectively transfer the load from the spinal column to the spinal stabilizer.

The invention also contemplates a spinal stabilizer including such a connection. The spinal stabilizer comprises an elongate member adapted to be affixed to a vertebra and defining a planar aperture. A washer is provided with engagement means adapted to engage the elongate member adjacent the periphery of the aperture at any of a plurality of relative rotational positions between the washer and the elongate member about a notional rotational axis that extends through the aperture, the washer having a passage therethrough, one end of the passage being located at a concave surface formed on the washer and communicating with the plane of the aperture and the other end of the passage being located at a bearing surface formed on the washer. A nut that is threaded onto a pedicle screw with a hemispherical head engages the bearing surface when the screw extends through the passage and the aperture to engage the vertebral body of the vertebra, the axis of the passage intersecting the plane of the aperture at a first angle and the bearing surface at a second angle, at least one of the angles being acute, the plane of the aperture being inclined relative to the bearing surface so that the angle of inclination of the screw extending through the passage is adjusted in dependence upon the relative rotational position between the washer and the elongate member and the hemispherical head of the pedicle screw and the concave surface of the washer providing effective transfer of the load from the patient's spinal column to the spinal stabilizer regardless of the angle of inclination.

In another aspect, the present invention contemplates a novel washer for use in connection with an internal spinal stabilizer that comprises a cylindrical body with a passage through the body which may optionally be offset from the center of the longitudinal axis of the washer. The passage receives a pedicle screw of a type known in the art having a hemispherical head and threads for receiving a nut for affixing an internal spinal stabilizer to the vertebral body of a patient. The body of the washer is provided with a bearing surface for the nut and a concave surface for engaging the hemispherical head of the screw. Means is formed on the body for rotatably engaging the spinal stabilizer to allow the body to rotate around the 360° of the hole to provide infinite variability in the angle and location of the interface between the screw and the plate, engagement of the hemispherical head and the concave surface, thereby providing effective transfer of the load from the spinal column to the spinal stabilizer regardless of the angle and location of the screw relative to the spinal stabilizer.

In another aspect, the present invention comprises a washer for use with an internal spinal stabilizer comprising a body defining means adapted to engage cooperating engagement means on a spinal stabilizer and a concave surface for engaging the hemispherical head of the screw with which the spinal stabilizer is affixed to the spinal column, the engagement means on the washer being adapted to engage the cooperating engagement means on the stabilizer at a plurality of points within a common plane and with the washer in any one of a plurality of relative rotational positions about an axis substantially perpendicular to the common plane relative to the stabilizer, a passage extending through the washer and defining an axis that intersects the common plane at a first predetermined angle at one end of the passage and a bearing surface against which the nut that threads onto the pedicle screw bears, the axis of the passage intersecting the plane of the bearing surface at a second predetermined angle, at least one of the first or second predetermined angles being an acute angle.

The present invention also provides a method of affixing a spinal stabilizer to the vertebra of a patient, the stabilizer comprising a washer with a bearing surface and a concave surface and having a passage therethrough, a cross-bar, and a pedicle screw having a hemispherical head and threads for receiving a nut thereon, comprising the steps of engaging the cross-bar with the washer, inserting the screw through the passage in the washer and affixing the screw to the vertebral body, and tightening the nut on the screw, the concave surface of the washer engaging the hemispherical head of the pedicle screw when the nut is tightened against the bearing surface to effectively transfer the load from the vertebra to the spinal stabilizer at any of a plurality of angles relative to the cross-bar.

It is also an aspect of the invention to proved a spinal stabilizer for affixing to the vertebral body of a patient comprising first and second elongate members attached to each other at an angle of approximately 90°, the second elongate member being rotatable about its longitudinal axis relative to the first elongate member, a washer, and means on the second elongate member for engaging the washer in any one of a plurality of relative rotational positions at a plurality of points within a common plane about an axis substantially perpendicular to the common plane.

In another embodiment, the present invention comprises a spinal stabilizer adapted for affixing to a vertebra of a patient with a pedicle screw that comprises first and second elongate members having slots formed therein with a bolt extending through the slots with a nut engaging the bolt. Means is formed on the bolt for retaining the bolt in one or the other of the slots formed in the first and second elongate members before the nut is engaged to the bolt, thereby preventing the bolt from dropping out of the stabilizer into the patient.

Referring now to the FIG. 1 of the drawings, there is shown a partially schematic, dorsal view of a portion of the human spinal column having a first preferred embodiment of a spinal stabilizer constructed in accordance with the teachings of the present invention surgically affixed thereto.

FIG. 10A is a top, perspective view of a fifth embodiment of a washer constructed in accordance with the teachings of the present invention.

FIG. 10B is a side, elevational view of the washer of FIG. 10A

FIG. 12 is a partially exploded, perspective view of a portion of a second embodiment of a spinal stabilizer constructed in accordance with the teachings of the present invention utilizing the washer of FIGS. 10A and 10B.

FIG. 13 is a side, elevational view of a portion of the cross-bar of the spinal stabilizer of FIG. 11.

FIG. 20 is a perspective view of a portion of the spinal stabilizer of FIG. 19.

FIG. 21 is a perspective view of a portion of the spinal stabilizer of FIG. 19.

FIG. 22 is also a perspective view of a portion of the spinal stabilizer of FIG. 19.

FIG. 24 is a perspective, partially exploded view of a portion of the spinal stabilizer of FIG. 23.

FIG. 25 is a bottom, perspective view of a sixth alternative embodiment of a washer constructed in accordance with the teachings of the present invention intended for use in connection with the spinal stabilizer of FIG. 24.

FIG. 26 is a side, elevational view of the washer of FIG. 25.

Figure 29:
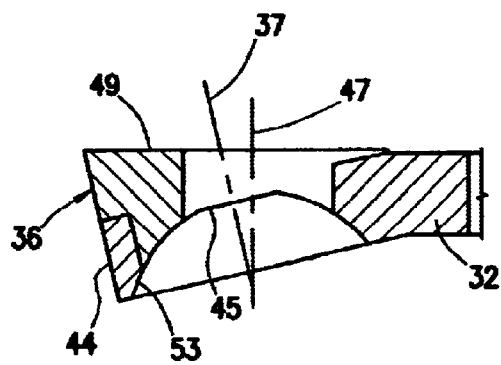
FIG. 29 is a sectional view through a portion of the cross-bar of the spinal stabilizer shown in FIGS. 1, 2, and 11 having the washer of FIGS. 4–6 engaging the cross-bar thereof to show the interaction between the concave surface of the washer and the opening through the cross-bar and the angle of the axis of the body of the washer.
Figure 30:
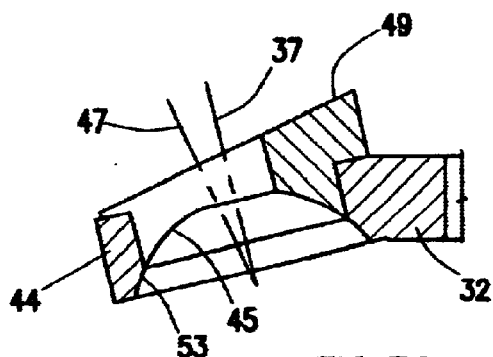
Figure 4:
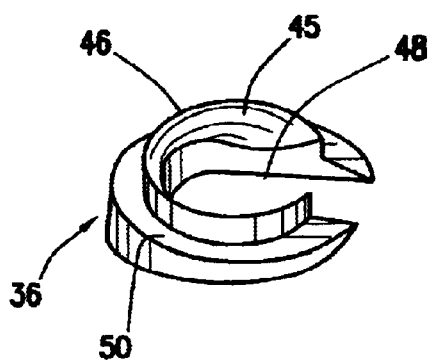
FIG. 4 is bottom, perspective view of a first embodiment of a washer constructed in accordance with the teachings of the present inventor.
Figure 5:
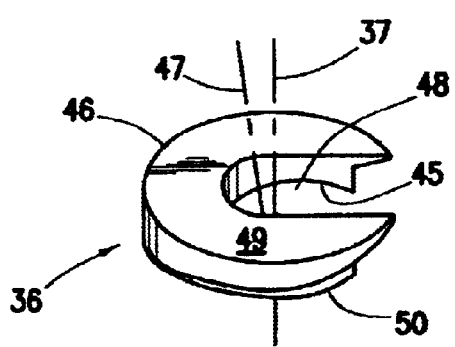
FIG. 5 is a top, perspective view of the washer of FIG. 4.
Figure 6:
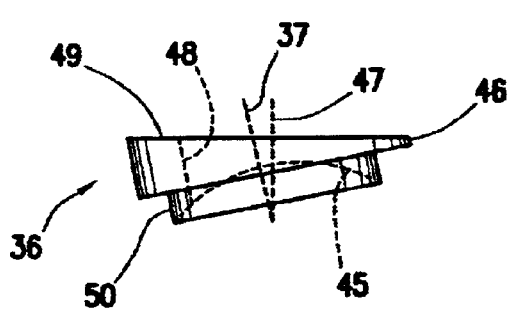
FIG. 6 is a side, elevational view of the washer of FIG. 4.
Figure 9:
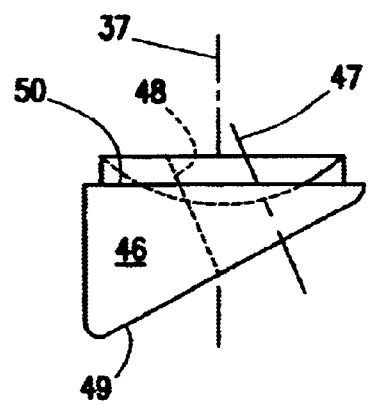
FIG. 9 is a side, elevational view of a fourth embodiment of a washer constructed in accordance with the teachings of the present invention.

FIG. 30 is a sectional view through a portion of the cross-bar of the spinal stabilizer shown in FIGS. 1, 2, and 11 again having the washer of FIGS. 4–6 engaging the cross-bar but with the washer rotated approximately 180° from the position shown in FIG. 29 to show that the interaction between the concave surface of the washer and the opening through the cross-bar is the same as in FIG. 29 but that the angle of the axis of the body of the washer is changed relative to the cross-bar of the spinal stabilizer.

FIG. 31 is a sectional view through a portion of yet another alternative embodiment of the spinal stabilizer of the present invention.

Figure 1:
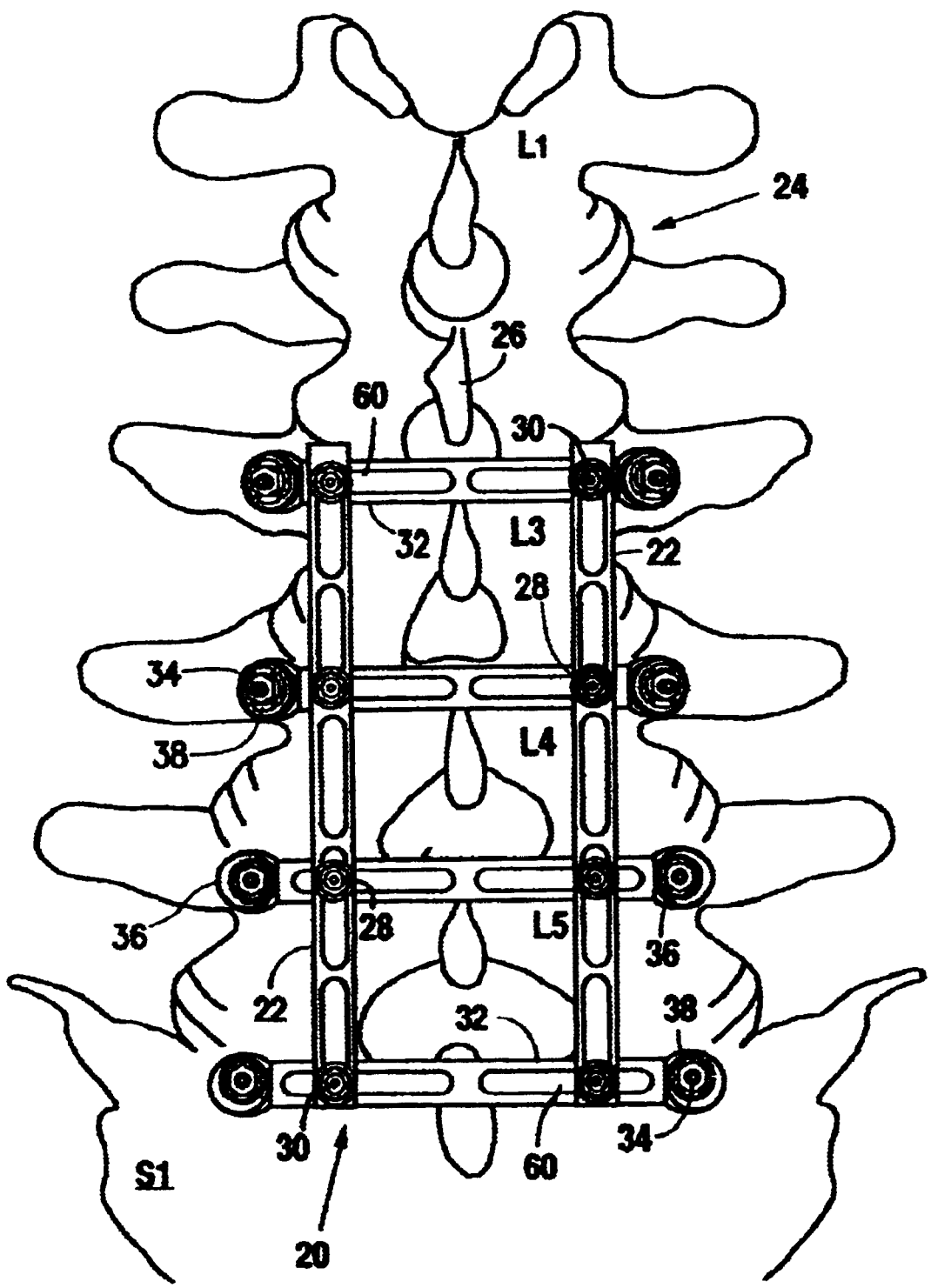
Figure 2:
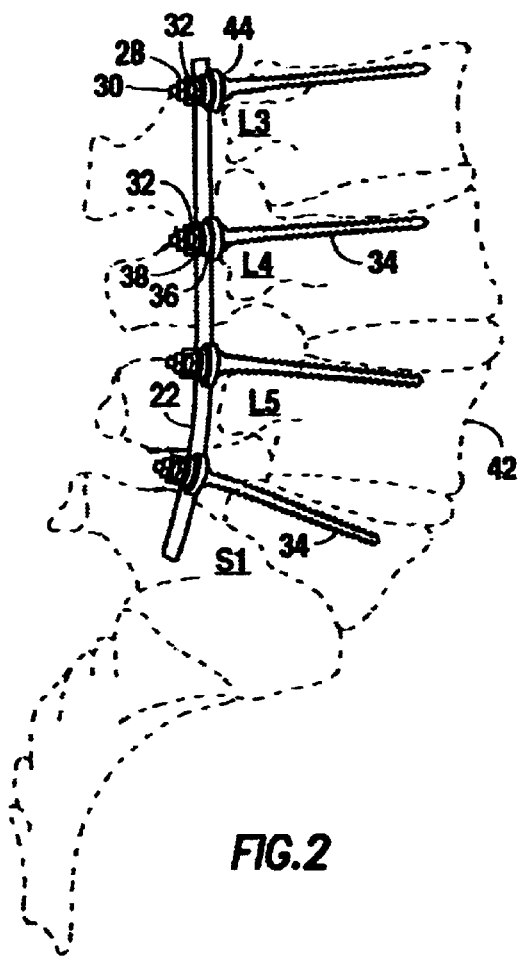
FIG. 2 is a lateral view of the human spinal column having the spinal stabilizer of FIG. 1 affixed thereto and showing the spinal column in phantom lines to show the many different positions and angles of the pedicle screws used to affix the spinal stabilizer to the spinal column.
Figure 11:
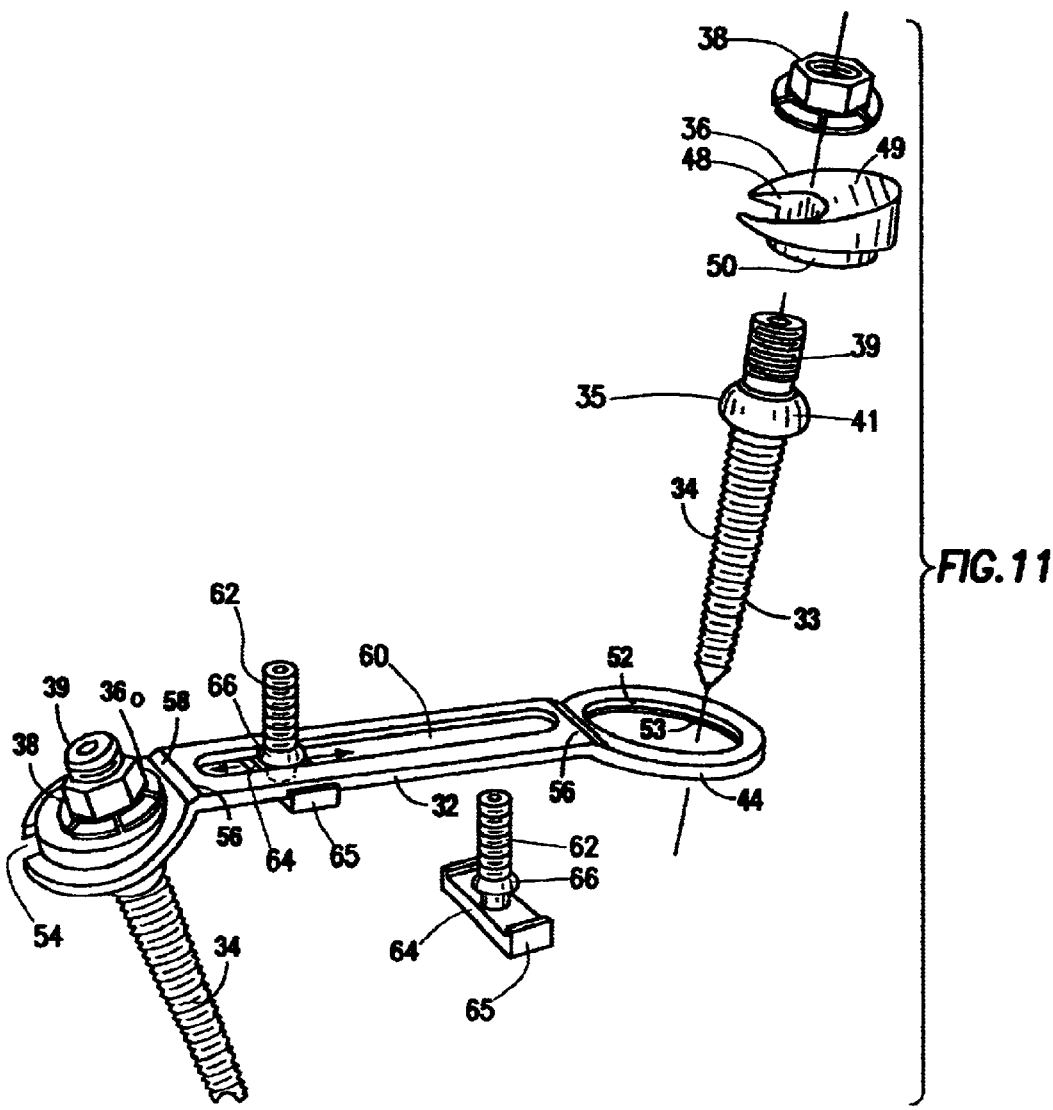
FIG. 11 is a partially exploded, perspective view of a portion of the spinal stabilizer of FIGS. 1 and 2 utilizing the washer of FIGS. 4–6.

Referring now to the figures, a first embodiment of a spinal stabilizer constructed in accordance with the present invention is shown affixed to the spinal column in FIGS. 1 and 2. This first embodiment, indicated generally at reference numeral 20, is comprised of a pair of first elongate members, or rods 22 oriented along the longitudinal axis of the spinal column 24 on either side of the spinous processes 26 of lumbar vertebrae L3–L5 and the first sacral vertebrae S1. Rods 22 are connected at the level of each vertebrae S1, L3–L5 by nut and screw 28 and 30 to a corresponding number of second elongate members that may comprise a rod, cross-bar, C-clamp, or plate, a cross-bar 32 being shown in FIGS. 1–2. The threaded portion of screws 30 is preferably of a type known in the art in which the portion of the screw threads projecting through nut 28 is broken off so as not to project any further from the nut 28 than needed. Each cross-bar 32 is affixed to the corresponding vertebrae by a pedicle screw 34, washer 36, and nut 38, screws 34 being anchored in the pedicle 40 (see FIG. 3) of each vertebrae. Screws 34, shown in more detail in FIGS. 11 and 12, are also of a type known in the art in which the bottom portion 33 is provided with threads for affixing to the vertebrae, a head 35 with a rounded, or hemispherical upper surface 41 (FIG. 11) or flat upper surface 43 (FIG. 12), and an upper threaded portion 39 for threadably receiving the nut 38, the portion of the upper threads 39 projecting through nut 38 being of the type that is broken off so as not to project any further through nut 38 than necessary. A screw of this type is shown, for instance, in U.S. Pat. No. 5,129,899, which patent is incorporated herein in its entirety by this specific reference thereto.

Figure 3:
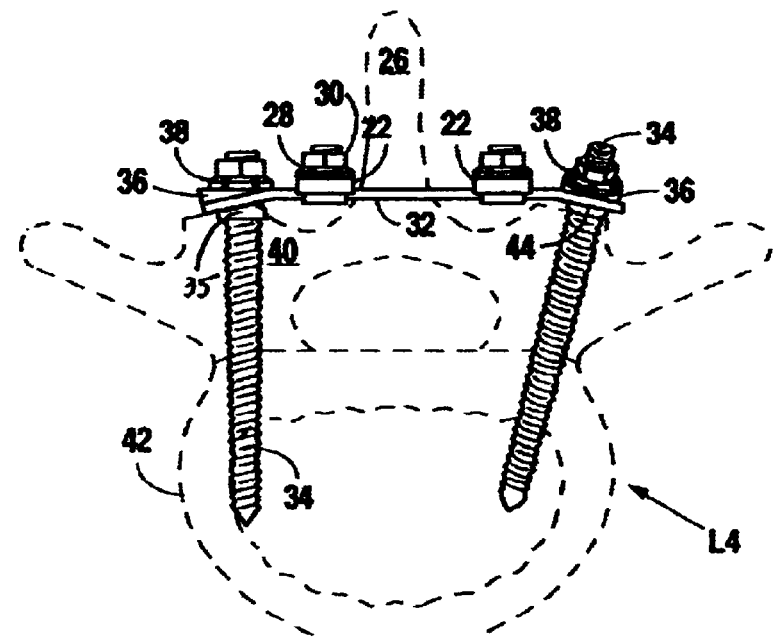
FIG. 3 is a top plan view of the spinal stabilizer of FIGS. 1 and 2 showing a lumbar vertebra (more specifically, L4) in phantom lines to show the positions and angles of the pedicle screws used to affix the spinal stabilizer to the spinal column.

As noted above, the need for secure anchorage of the screws 34 in the vertebrae, the lordosis of the spine and corresponding curve in rods 22 (best shown in FIG. 2), inward angle of the screws 34 (best shown in FIG. 3), different sizes, spacing, and shapes of the vertebral bodies 42, and many other factors (including the particular pathology which the spinal fixation system is intended to address), require that almost every screw 34 be affixed to the corresponding vertebra at a unique angle relative to rods 22. To illustrate, in FIGS. 1–3, it can be seen that each screw is angled in three axes of a three-dimensioral coordinate system (not shown) having its origin on the center axis of the spinal column 24. If the Y coordinate of the coordinate system is coincident with the center of the longitudinal axis of the spinal column 24 (such that +Y is anterior and –Y is posterior), the X coordinate is the lateral dimension, and the Z coordinate is orthogonal to the plane of the paper in FIG. 1 (such that +Z is ventral and –Z is dorsal), it can be seen in FIG. 2 that the positions of the tips of the screws 34 are defined by Y and Z coordinates. Reference to FIG. 3 (in which the Y coordinate of the hypothetical coordinate system runs in and out of the plane of the paper) illustrates that the positions of the tips of the same screws are also defined by an X coordinate. Also in FIG. 3, it can be seen that the ends 44 of cross-bar 32 are angled downwardly, or ventrally (relative to the body of the patient), to accommodate the round shape of the body 42 of the vertebrae L4 to which the cross-bar 32 is affixed by screws 34. Although the cross-bar 32 need not be shaped in this fashion, this bend at the ends 44 of cross-bar 32 serves several advantages other than accommodating the shape of the vertebral body (for instance, reducing the height of the stabilizer in the direction of the Z coordinate of the three-dimensional coordinate system described above) and is therefore particularly adapted for use in the spinal fixation system of the present invention. However, the downward bends at the ends 44 also introduces yet another angle into the interface between the screw 34 and the cross-bar 32. As a result of the angle of the screw 34 and the bend at the end 44 of cross-bar 32, the longitudinal axis of screw 34 is unlikely to be perpendicular to the plane of the surface of cross-bar 32 at the connection between the screw 34 and cross-bar 32, and therefore unlikely to optimally transfer load from the spinal column 24 to the spinal stabilizer 20.

Figure 7:
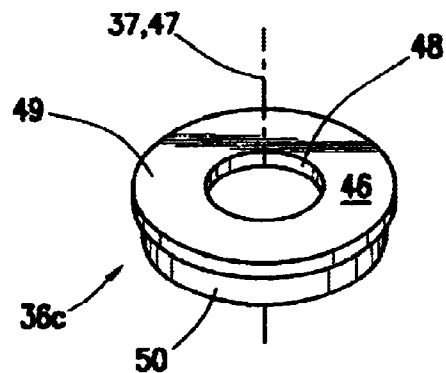
FIG. 7 is a top, perspective view of a second embodiment of a washer constructed in accordance with the teachings of the present invention.

To address this load transfer problem, FIGS. 4–10 and 25–28 show a plurality of washers 36 constructed in accordance with the teachings of the present invention that are shaped and/or configured to provide optimal load transfer from the spinal column 24 to the spinal stabilizer 20 through pedicle screw 34. The washer 36 shown in FIGS. 4–10 is comprised of a cylindrical body 46 having a longitudinal passage 48 therethrough for receiving the screw 34 for affixing the spinal stabilizer 20 to the vertebral body 42. The passage 48 communicates with, or opens to, a concave surface 45 and a bearing surface 49, the concave surface 45 being adjacent the shoulder 50 in each of the washers 36 shown in FIGS. 4–9 and 25–26. In the alternative embodiment of the washer 36 shown in FIGS. 10A and 10B, the bearing surface 49 is adjacent the shoulder 50. The longitudinal center axis 47 of the passage 48 through the body 46 the alternative embodiment of the washer 36, shown in FIG. 7 is centered on the longitudinal enter axis (represented by the phantom line 37 in FIG. 7) of washer $36_c$ and the center axis 47 of the passage 48 in the body 46 of washer $36_o$ (FIG. 8) is offset from the longitudinal center axis 37 of the washer $36_o$ for a purpose to be described below.

Each of the washers 36 shown in FIGS. 4–10 and 25–28 is also provided with means formed on the body 46 for rotatably engaging the spinal stabilizer 20. This engagement means takes several forms; in the embodiment shown in FIGS. 4–10, the stabilizer engaging means comprises a shoulder 50 formed on the body 46 of the washer 36 for engaging the cross-bar 32 (not shown) adjacent the periphery of the aperture 52 formed in the ends 44 of cross-bar 32 when the washer 36 is assembled to the cross-bar 32 in the manner described below. In the embodiment shown in FIGS. 25 and 26, showing yet another embodiment of the washer 36, the engaging means comprises a recess 112 shaped to engage the complimentary-shaped boss 110 formed around the periphery of the aperture 52 formed in the ends of the cross-bar 32 of the embodiment of the stabilizer shown in FIG. 24. In the embodiments shown in FIGS. 27–28, the engagement means takes the form described below.

Those skilled in the art will recognize that the stabilizer engaging means need not be comprised of the shoulder 50 (FIGS. 4–10) or recess 112 (FIGS. 25–26). In a third embodiment (not shown), the stabilizer engaging means takes the form of three or more radially outwardly extending projections on the surface of the walls of the body 46 (the "O.D." of the body) which, when body 46 is inserted through the aperture 52 in the ends 44 of cross-bar 32, creates an interference with the periphery of aperture 52 so that the washer 36 effectively sits in the aperture 52 with the projections on the O.D. of the body acting as a spider engaging the periphery of aperture 52 to support the washer in the aperture 52. Alternatively, and particularly in the case of the washers shown in FIGS. 6–10 described below, the O.D. of the body 46 of washer 36 is provided with a groove and the washer is inserted with the angled bearing surface 49 (see below) up from beneath the aperture 52 in the ends 44 of cross-bar 32 and rotated so that the groove engages and interacts with the periphery of the aperture 52 so as to limit the travel of the washer through the aperture 52. In another embodiment, the stabilizer engaging means takes the form of a plurality of projections projecting radially inwardly from the periphery of the aperture in the cross-bar for engaging a shoulder or slot formed on the O.D. of the body of the washer. In yet another embodiment, the washers are comprised of a resilient material such as a medical grade polymeric material which are provided with a groove formed on the O.D. thereof which is press-fit into the aperture 52 in cross-bar 32.

Note also that, although the several embodiments of washer 36 shown herein take the form of a right angle cylinder, it is not required that the washer 36 take that form. To facilitate rotation of washer 36 relative to cross-bar 32 for a purpose made clear below, both the aperture 52 in cross-bar 32 and the washer 36 engaging the periphery of the aperture are conveniently circularly shaped. However, the body 46 of washer 36 can also be square, pentagonal, hexagonal, octagonal, etc. in shape while still allowing the washer 36 to rotate in aperture 52, for instance, by making the body 46 of washer 36 square and the shoulder 50 on the square body round. A washer with a square body provides the additional advantage of providing flat surfaces against which a wrench can bear to allow forceful rotation of the body for optimal angulation of the pedicle screw 34 relative to the cross-bar 32 of stabilizer 20. Similarly, substantially the same result as described herein can be achieved by making the body 46 and shoulder 50 of washer 36 hexagonal or octagonal and the aperture 52 in the ends 44 of cross-bar 32 hexagonal or octagonal for receiving a hexagonally- or octagonally-shaped shoulder 50. Although such a washer could not be rotated relative to cross-bar 32 once assembled to the pedicle screw 34 and after the nut 38 is tightened, until the nut 38 is tightened, a hexagonally- or octagonally-shaped washer can be backed out of the corresponding hexagonally- or octagonally-shaped aperture and rotated one-sixth or one-eighth of a rotation in either direction, thereby effectively functioning in the same way as a washer with a cylindrical body 46 to achieve the same result of optimal load transfer from screw 30 to the cross-bar 32 of the spinal stabilizer. Such embodiments have the additional advantage of not allowing rotation of the washer 36 relative to the spinal stabilizer once the nut 38 is tightened, thereby providing additional structural rigidity to the spinal stabilizer once it is affixed to the spinal column of the patient. In contemplation of the manner that these additional shapes function in substantially similar way to achieve a substantially similar result as the preferred embodiment, the washer of the present invention is referred to herein as being "substantially cylindrical" rather than requiring that it be "cylindrical."

Figures 27, 28:
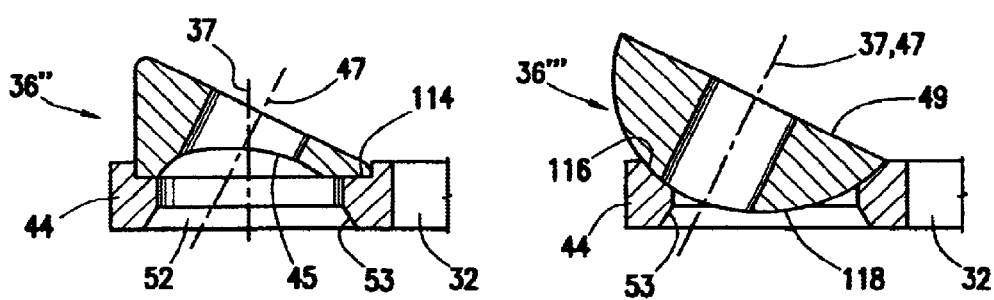
FIG. 27 is a sectional view through a portion of the cross-bar of another embodiment of the present invention having a seventh alternative embodiment of a washer constructed in accordance with the teachings of the present invention engaged thereto.
FIG. 28 is a sectional view through a portion of the cross-bar of yet another embodiment of the present invention having an eighth alternative embodiment of a washer constructed in accordance with the teachings of the present invention engaged thereto.

Further, as noted above, the engaging means need not be exclusively located on just the washer to fall within the scope of the present invention. In the embodiment shown in FIGS. 24–28, the aperture 52 is provided with either a raised boss 110 for engaging either a recess 112 in the bottom surface of the washer $36_o$ 'shown in FIGS. 25–26 or a shoulder 114 (see the left side of FIG. 24) for receiving the body of a washer 36" with straight sides as shown in FIG. 27. In another embodiment shown in FIG. 28, the aperture 52 of the cross-bar 32 is provided with a dished surface 116 for engaging the convex bottom surface 118 of the washer 36''' shown in FIG. 28. Alternatively, the inside edges of the aperture 52 are beveled and the bottom edge of the washer is provided with a complimentary bevel for engaging the washer. All such embodiments, and others functioning to allow the washer to engage the aperture in the cross-bar at a plurality of points within a common plane in any of a plurality of rotational positions relative to the spinal stabilizer which may be developed by those skilled in the art who have the benefit of this disclosure, are considered equivalent to the structure disclosed herein and are therefore considered to be constructed in accordance with the present invention.

Figure 8:
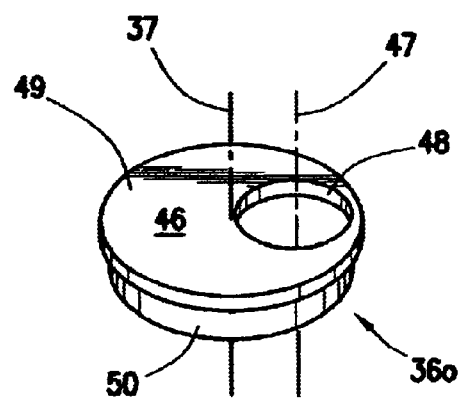
FIG. 8 is a top, perspective view of a third embodiment of a washer constructed in accordance with the teachings of the present invention.

Referring again to the several embodiments of the washer 36 shown in FIGS. 4–10, it can be see that the axis 47 of the passage 48 in the cylindrical body 46 of washer $36_c$ shown in FIG. 7 is centered on the longitudinal axis (represented by phantom line 37 in FIGS. 7 and 8) of washer $36_c$ and the axis 47 of passage 48 in the cylindrical body 46 of washer 36. in FIGS. 8 is offset from the center of the longitudinal axis (represented by phantom line 37 in FIG. 8) of washer $36_o$. The bearing surface 49 of washers 36 shown in FIGS. 4–6 and 9–10 is angled at an angle other than 90° relative to the side walls of the cylindrically-shaped body 46, giving the body 46 a wedge shape. As a result of the angled bearing surface 49 of body 46, the axis 47 of the passage 48 through washer 36 shown in FIGS. 4–6 and 9–10 is not parallel to the longitudinal axis 37 of the body 46 (best shown in FIGS. 9–10 in which the angle of the bearing surface 49 relative to the side walls of body 46 is more pronounced than the angle of the bearing surface 49 of the washers shown in FIGS. 4–6).

The bodies 46 of the washers 36 are described as being substantially cylindrical for the reason described above and to provide a basis for referring to the longitudinal axis of the washer 36 even though it will be recognized that the height of the right angle cylinder defined by the washers of FIGS. 4–8 is minimal since the washers shown in FIGS. 4–8 are accurately described as "flat washers." However, as set out above, one end 49 (defining the bearing surface against which the nut 28 threaded onto screw 34 is tightened to affix the spinal stabilizer to the vertebra) of the bodies 46 of the washers 36 shown in FIGS. 4–6 and 9–10 is angled relative to the side walls of the generally cylindrically-shaped body 46 of washer 36. In the embodiments shown in FIGS. 7 and 8, the bearing surface 49 is angled at an angle of approximately 90° such that the washers shown in those figures are flat, but the bearing surface 49 of the bodies 46 of the washers 36 shown in FIGS. 4–6 and 9–10 is angled relative to the side walls at an angle other than 90° such that the bodies 46 of washers 36 shown in those figures have a substantial vertical dimension and are wedge-shaped rather than flat. A variety of angles may be utilized to advantage, but angles (relative to the side walls of the cylindrically-shaped body 46) ranging from about 7.5° to about 30° have generally proven to be adequate to provide a full range of adjustability.

Referring now to FIGS. 10A and 10B, an alternative embodiment of the washer of the present invention is shown. The washer 36 shown in FIGS. 10A and 10B is similar to the washers shown in FIGS. 4–6 and 9, but is provided with a concave bearing surface 49 for interaction with a nut 38 (not shown in FIGS. 10A and 10B but visible in, for instance, FIGS. 1–3) having a convex lower surface. When the nut 38 threaded onto pedicle screw 34 is tightened against the washer 36 shown in this figure, the concave upper surface 49 provides an even greater range of angles and adjustability of placement of the screw 34 relative to the spinal stabilizer 20. Because the end surface 49 is the end surface of the body 46 comprising washer 36 against which the pedicle screw 34 bears, it is referred to herein as the bearing surface 49 of washer 36.

As best shown in FIGS. 3 and 11, washers 36 rotatably engage cross-bar 32 at the ends 44 thereof As described above, in the embodiment shown, rotatable engagement is accomplished by resting the shoulders 50 of washers 36 comprising the preferred stabilizer engaging means on the margins of the apertures 52 at the ends of cross-bars 32. During the surgical procedure, the surgeon selects either a flat washer with a longitudinal passage coincident with the center of the longitudinal axis of the washer (FIG. 7), a flat washer with a passage offset from the center of the longitudinal axis of the washer (FIG. 8), a wedge-shaped washer with a passage coincident with the center of the longitudinal axis of the washer (FIGS. 4–6 or 27), or a wedge-shaped washer with a passage offset from the center of the longitudinal axis of the washer (FIGS. 9, 10A, 10B, 25, and 26), and then rotates the body 46 of the washer 36 select A in the aperture 52 to provide infinite adjustability of the linkage between the cross-bar 32 and screw 34, regardless of the angle and position of the screw 34 in the pedicle 40 of each vertebrae and regardless of the shape, size, or pathology of the vertebrae and/or pedicle. For even more adjustability, a washer with a concave bearing surface 49 or a rounded bottom (for engagement of an aperture having dished surface 116 as shown in FIG. 28) is utilized. The washer selected is preferably the washer which, by its shape and ability to be rotated, locates the passage therethrough in the proper position for receiving the screw 34 while maintaining an angle of approximately 90° between the longitudinal axis of the screw 34 and the bearing surface 49 of the washer against which the nut 38 bears when tightened to effectively transfer oad from the spinal column 24 to the implant 20. It will be noted that when the screw 34 engages the bearing surface 49 of washer 36 and extends through the passage 48 and the aperture 52 to engage the vertebra, the axis 47 of passage 48 intersects the plane of the aperture at a first angle and, depending on whether the bearing surface 49 is inclined, or angled, the rotational position of the washer relative to the spinal stabilizer, may intersect the bearing surface 49 at a second angle, but that at least one of the first or second angles must be an acute angle.

To facilitate assembly of cross-bar 32 to screws 34, one end 44 of cross-bar 32 may be provided with a gap or break 54 through which the portion of the screw 34 protruding from the pedicle is maneuvered. Regardless of how screw 34 is placed in the aperture 52 in cross-bar 32, when nut 38 is tightened against bearing surface 49, the underside of cross-bar 32 and the concave surface 45 of washer 36 are tightened against the hemispherical surface 41 of the head 35 of screw 34, the beveled surface 53 on the underside of the periphery of aperture 52 and the concave surface 49 of washer 36 providing a substantially continuous, stable bearing surface for engaging the hemispherical surface 41 with the axis 47 of the passage 48 through the body 46 of the washer 36 (and the longitudinal axis of screw 34) at any of an infinite number of angles relative to the cross-bar 32 of stabilizer 20. The head of screw 34 is sized so as to contact the margin of aperture 52 in cross-bar 32, the bevel 53 and hemispherical upper surface 41 of the screw 34 helping to center the longitudinal axis of aperture 52 in cross-bar 32 on the longitudinal axis of screw 34.

This functional relationship between the bevel 53 around the periphery of aperture 52 and the concave surface 45 of washer 36 is best shown in FIGS. 29 and 30, in which the washer 36 is rotated approximately 180° between the two figures to change the axis of the passage 48 to accommodate a screw (not shown) at two different angles relative to cross-bar 32. Because the hemispherical surface 41 of the head 35 of screw 34 engages both the cross-bar 32 (around the periphery of aperture 52 at the bevel 53) and the concave surface 45 of washer 36 at any angle between screw 34 and stabilizer 20, the load of the patient's spinal column 24 is effectively transferred from the spinal column 24 to stabilizer 20, regardless of the geometry between the screw and the stabilizer.

FIG. 11 shows the interaction and adjustability of the spinal stabilizer of the present invention by showing one of the two pedicle screws 34 to which nut 38 is tightened against the wedge-shaped washer 36 of FIGS. 4–6 with the washer $36_o$ having been rotated relative to cross-bar 32 in the common plane formed by the cooperating engaging means on the washer and the cross-bar 32 of the spinal stabilizer so that the screw 34 is angled anteriorially (with reference to the patient) while also being angled inwardly (relative to the central axis of the spinal column 24). A second washer 36 is shown on the other side of the cross-bar 32 which has been rotated so that the screw 34 is not centered in the aperture 52 of cross-bar 32 and the inward angle of the screw resulting from the downward bend at the ends 44 of cross-bar 32 is maintained. Cross-bar 32 is shown with an optional nipple 56 forming a stop surface 58 near the apertures 52 therethrough which acts, by engagement of the O.D. of the washer 36, to restrain any tendency of the washer 36 to move inwardly from the ends 44 of cross-bar while the nut 38 is being tightened against the washer 36 when in place in the aperture 52 in cross-bar 32.

The screw 34 in FIG. 12 is provided with a flat upper surface 43 on the head 35 and the bottom surface 51 of the washer 36 is flat as shown in FIGS. 10A and 10B. In this embodiment, the bearing surface 49 is concave and the infinite number of angles between the longitudinal axis of screw 34 and cross-bar 32 results from the positioning of the nut 38 in the "dish" formed by the concave bearing surface 49 of washer 36 and the rotation of washer 36 in the common plane of the aperture 52 at which the cross-bar 32 is engaged at a plurality of points to any of a plurality of rotational positions relative to the cross-bar 32 of the spinal stabilizer 20 allows the angling of screw 34 as needed to accommodate the particular operating environment. In the event of an extreme angle between screw 34 and cross-bar 32, and as noted above, the inside edge of cross-bar 32 is beveled as shown at reference numeral 53 in FIG. 13 to provide clearance for the screw 34.

Referring briefly again to FIG. 1, both the portion of the cross-bars 32 intermediate the ends 44 and the rods 22 are provided with longitudinal slots 60 for receiving the screws 30 for securing the rods 22 to cross-bars 32. Alternatively, either or both of the rods 22 and cross-bars 32 are provided with a plurality of nested slots (not shown) of a type known in the art (see, for instance, U.S. Pat. No. 4,696,290 and the so-called VSP spinal fixation system described in J. W. Brantigan, et al., Posterior lumbar interbody fusion technique using the variable screw placement spinal fixation system, in D. M. Arnold and J. E. Lonstein (Eds.), 6 State of the Art Reviews—Spine: Pedicle Fixation of the Lumbar Spine 201–234 (Philadelphia: Nanley & Belfus, Inc.) 1992; both references being hereby incorporated in their entirety by this specific reference thereto) for precise placement of the screws 30 securing the rods 22 to the cross-bars 32 along the longitudinal axis of cross-bar 32. The posts 62 of the screws 30 for securing the rods 22 to the cross-bars 32 are of the above-described type known in the art in which the portion of the post 62 that extends above the top of the nut 28 is broken off after the nut is tightened.

The screws 30 are shown in more detail in FIG. 11. Each screw is comprised of a post 62, "T"-shaped head 64, and bulge 66. The bulge 66 functions to retain the screw 30 in slot 60 when pressed up through the slot 60 to facilitate assembly of the rod 22 to the cross-bar 32 in the operating without losing the screw 30 down into the patient. In one embodiment, the inside edge of the slot 60 in cross-bar 32 opens upwardly with a flare, e.g., the surfaces, of sides, of the slot 60 are not parallel so that the screw 30 win slide easily from side-to-side in slot 60 once press fit into the slot. Alternatively, screw 30 or cross-bar 32 is comprised of a resilient, bio-inert material that allows passage of the screw 30 upwardly through slot 60 in cross-bar 32 but resists passage back in the other direction so that the screw 30 does not fall out of the slot 60. To further facilitate assembly of rod 22 to cross-bar 32 in the operating theater, the wings 65 of the "T"-shaped head 64 are dimensioned so that the wings 65 engage the outside edges of cross-bar 32 to prevent relative rotation between screw 30 and cross-bar 32 so that the nut 28 can be threaded onto the post 62 of screw 30 and tightened.

By comparison to FIG. 11, it can be seen that in the embodiment shown in FIG. 12, the attachment between rods 22 and cross-bars 32 is accomplished by tightening nuts 28 to the posts 62 integrally mounted to the plate 64 which moves from side to side along the longitudinal axis of cross-bar 32 in the slot 60 formed therein. The plate 64 is comprised of a flat portion (not visible in FIG. 12 because of the perspective in the figure) which extends under the cross-bar and which is tightened against the underside of cross-bar 32 when the nut 28 is tightened against a rod 22 to prevent further side to side movement of the plate 64 and post 62. Alternatively, the plate 64 is pre-assembled to the cross-bar 32 in slot 60 by press-fitting the plate 64 into a groove (not shown) or similar structure formed in the inside surface of the slot 60 in cross-bar 32 for sliding from side-to-side in the slot. Before tightening the nut 28, the plate is moved by the surgeon to the position that allows precise alignment of the rod 22 with the cross-bar 32.

Figure 14:
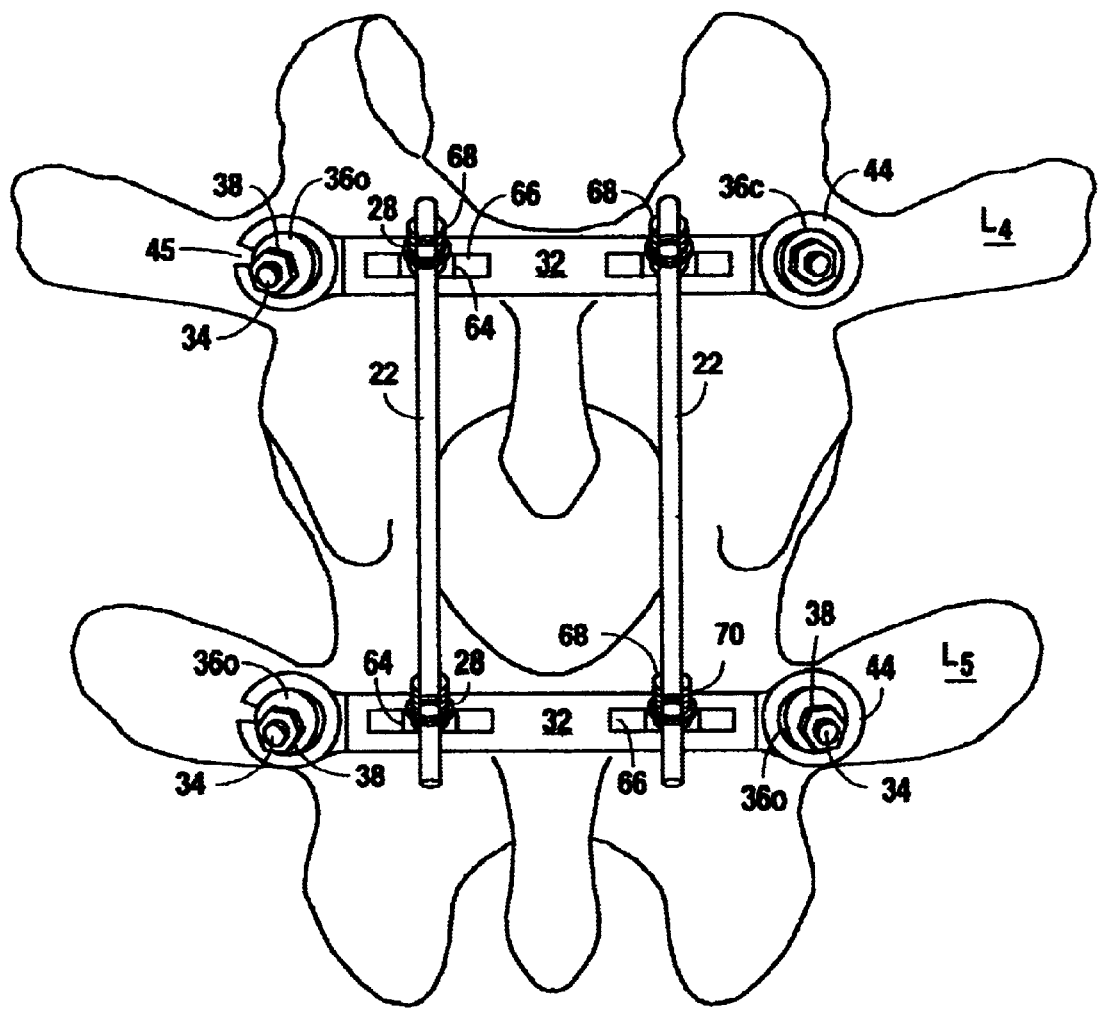
FIG. 14 is a partially schematic, dorsal view of a portion of the human spinal column having a third embodiment of a spinal stabilizer coistricted in accordance with the teachings of the present invention surgically affixed thereto.
Figure 15:
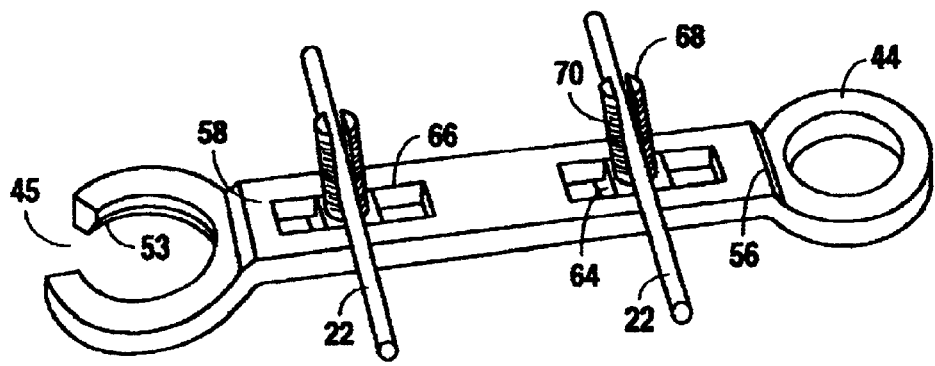
FIG. 15 is a perspective view of the cross-bar of the spinal stabilizer of FIG. 14.

In the embodiment shown in FIGS. 14–15, the rods 22 are of a type known in the art such as those available from MOSS® Miami (Cat. No. 1745–70, -72, and -74) that are attached to cross-bars 32 by U-shaped connectors 68 having threads 70 formed on the outside surfaces thereof For purposes of convenience, the rods 22 may be referred to generically as first elongate members and the cross-bars 32 are referred to a second elongate members. Connectors 68 are integrally mounted to a plate 64 having a construction similar to that of the so-called axial connectors available from MOSS® Miami (Cat. No. 1745–61 and -62), e.g., two halves (not shown) with threaded posts and nuts for connecting the halves on the top and bottom of the cross-bar 32 to clamp the cross-bar 32 And prevent side to side movement of the plate 64 in the slot 66 in cross-bar 32 in which the plate 64 moves. Alternatively, the plate 64 is provided with a portion extending under cross-bar 32 which is tightened against the underside of cross-bar 32 when the nut 28 is tightened on connector 68 to resist further side to side and/or rotational movement as described above.

Those skilled in the art will recognize from this description of the connectors 68 and plates 64 that a similar arrangement may be used in place of the nested slots 60 in the cross-bar 32 of the embodiment shown in FIG. 1 wherein the threaded posts 62 are replaced by connectors 68 for precise lateral placement of the point at which the rods 22 are attached to cross-bars 32. In such an embodiment, connectors 68 are provided with a head for engaging the underside of the cross-bar 32 in the same manner as the screws 30.

Figure 16:
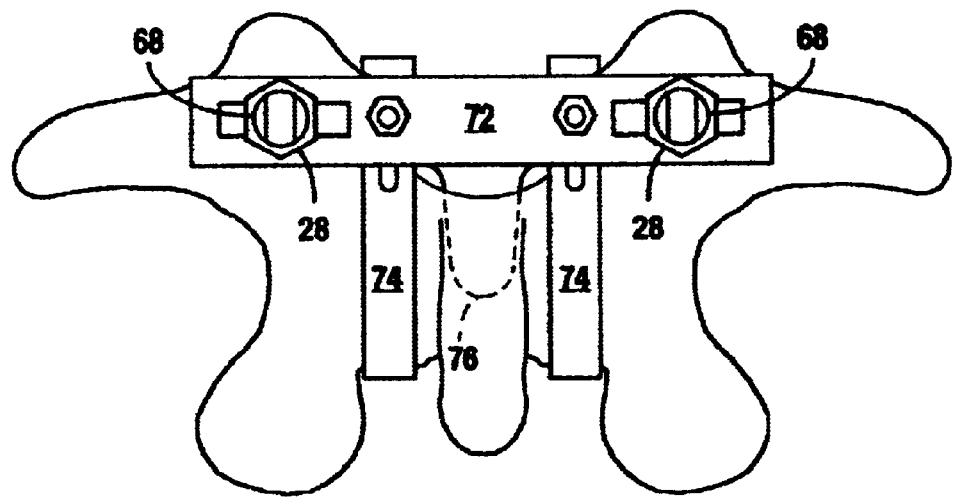
FIG. 16 is a dorsal view of a single lumbar vertebrae showing an alternative embodiment of a cross-bar constructed in accordance with the teachings of the present invention affixed thereto for use in connection with the spinal stabilizer of FIG. 14.
Figure 18:
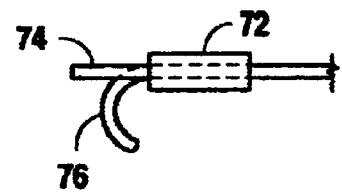
FIG. 18 is a detailed, side elevational view of a portion of the cross-bar of FIG. 16.
Figure 17:
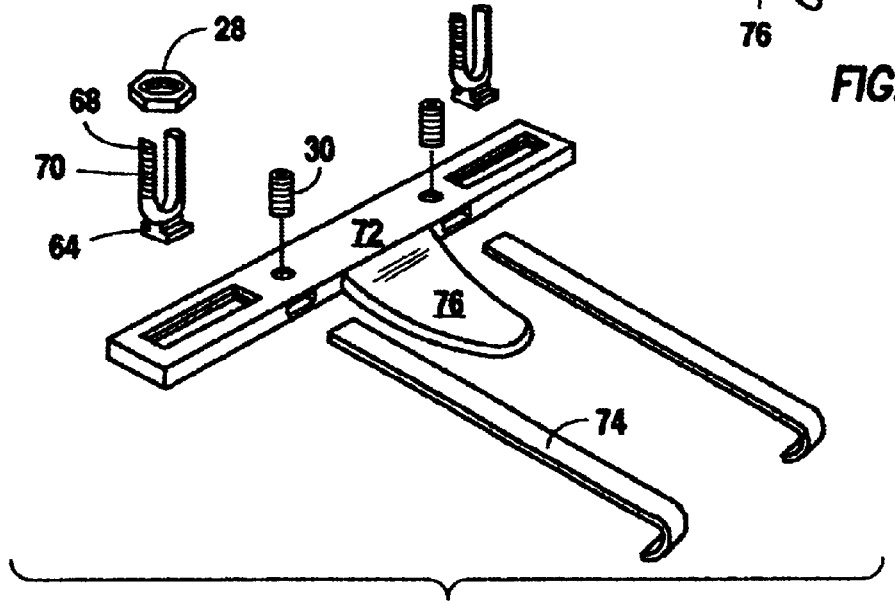
FIG. 17 is an enlarged, exploded perspective view of the cross-bar of FIG. 16.
Figure 19:
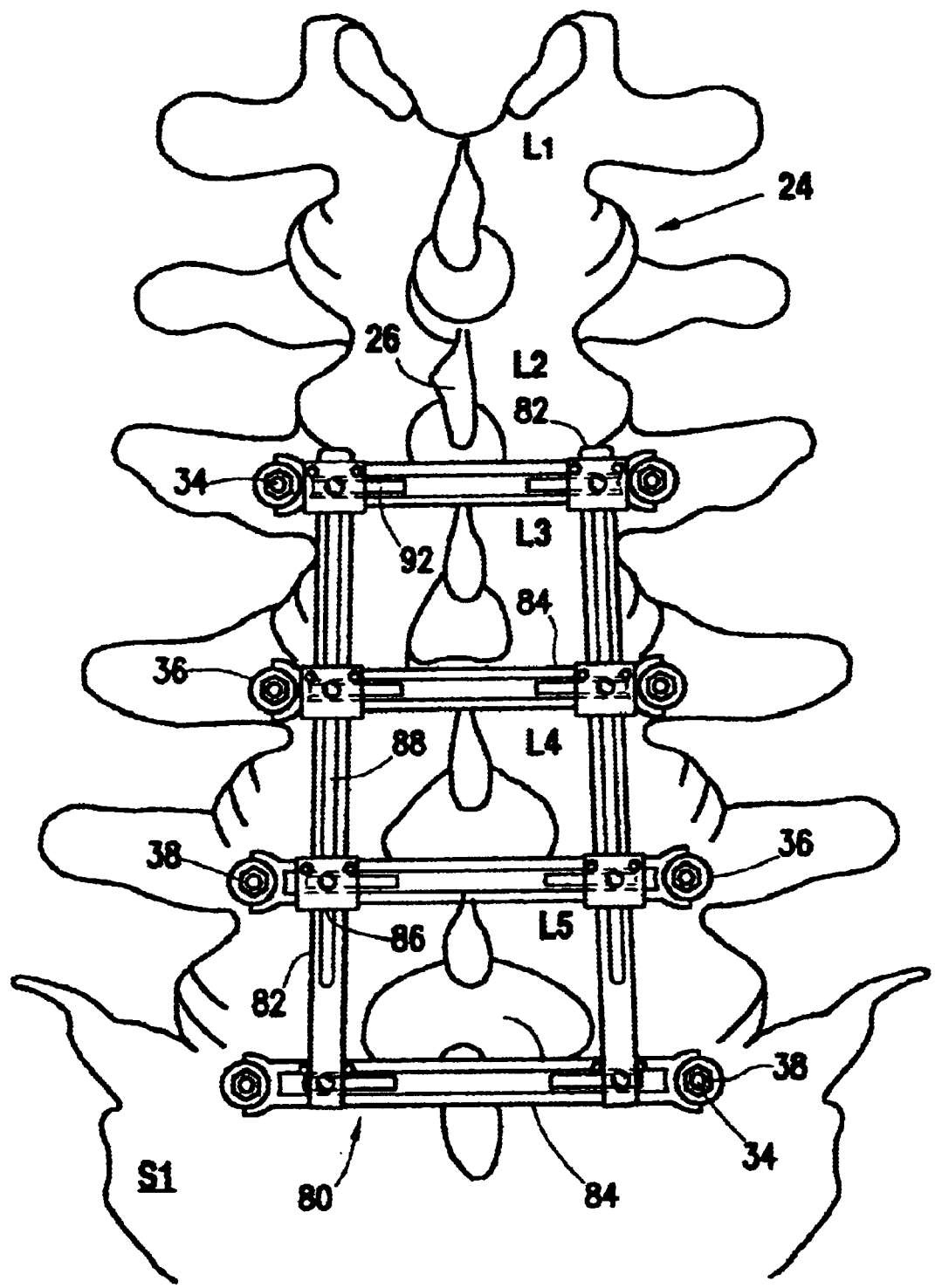
FIG. 19 is a partially schematic, dorsal view of a portion of a human spinal column having a fourth embodiment of a spinal stabilizer constructed in accordance with the present invention affixed thereto.
Figure 23:
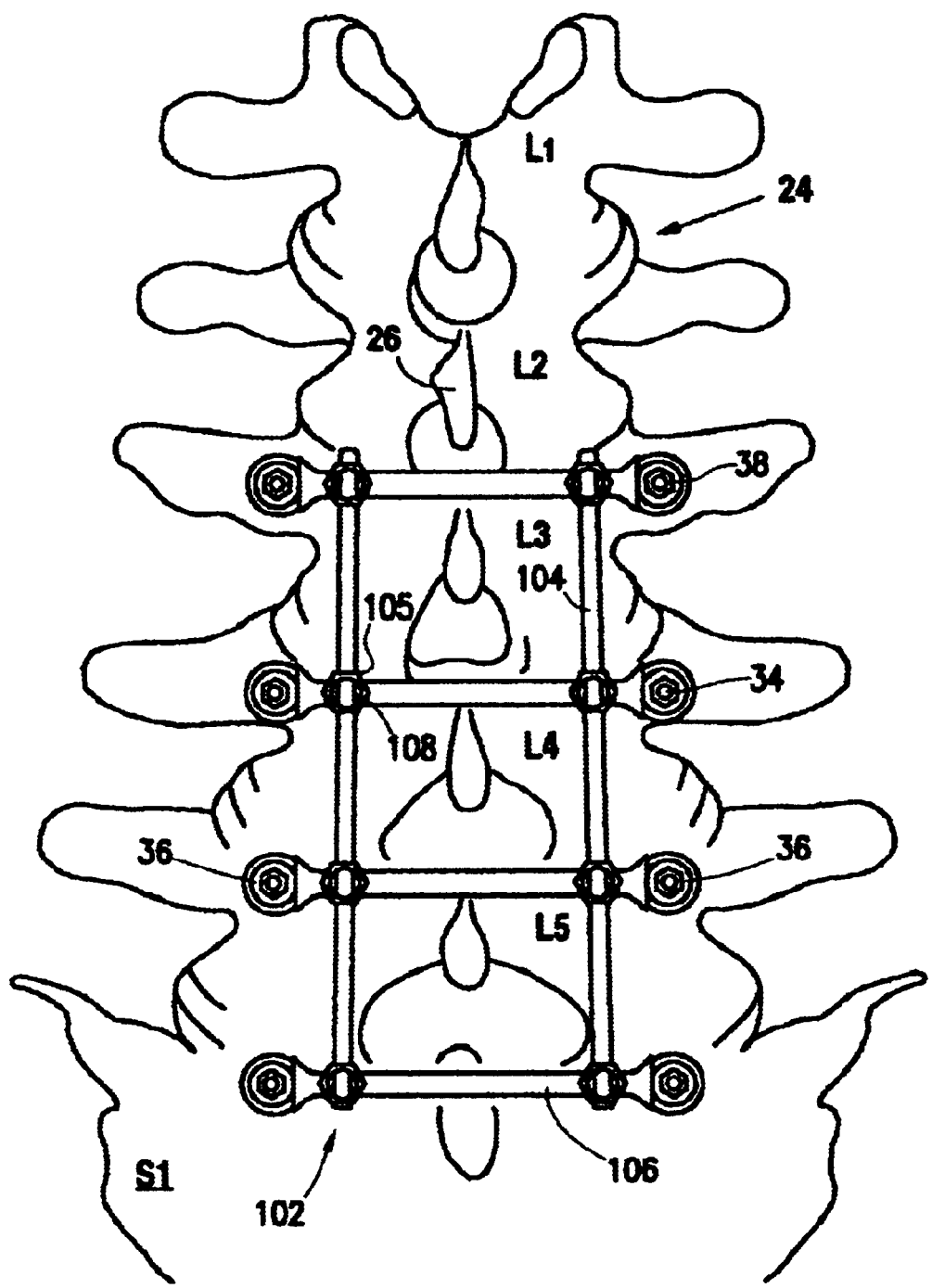
FIG. 23 is a partially schematic, dorsal view of a portion of a human spinal column having a fifth embodiment of a spinal stabilizer constructed in accordance with the present invention affixed thereto.

Referring now to FIGS. 16–18, the second elongate member comprises a cross-bar 72 of a type modified for use in connection with the embodiment lent of the spinal stabilizer of the present invention shown in FIGS. 14–15. The cross-bar 72 is provided with hooks 74 for engaging the lamina of the vertebra and a retainer 76 which is curved so as to extend under the lamina to which cross-bar 72 is to be affixed. The hooks 74 extend through a slot (not numbered for the sake of clarity) formed at approximately a right angle to the longitudinal axis of cross-bar 72 and are extended in and out of that slot until they are adjusted so as to tightly engage the posterior margin of the lamina and then set in that position by tightening the set screw 78 provided in cross-bar 72 for that purpose. U-shaped connectors 68 mounted on plates 64 as described above are provided for connecting to a rod 22 as shown in FIGS. 14–15.

Another embodiment of a spinal stabilizer constructed in accordance with the present invention is shown in FIGS. 19–22. In this embodiment, indicated generally at reference numeral 80, both the rods and cross-bars of the spinal stabilizer are formed in the shape of flat, elongate members, and are therefore referred to as first and second elongate members 82 and 84, respectively. First and second elongate members 82 and 84 are attached to each other at an angle of approximately 90° by the interaction of the brackets 86, slots 88, raised ridges 90, gutters 92, guide screws 94, and set screws 96. In more detail, the first and second elongate members 82 and 84 are assembled to each other by placing a second elongate member 84, which functions in the manner of the cross-bar 32 in the embodiments shown in FIGS. 1–3 and 12–15, into the "L" 98 of first elongate member 82 and tightening the guide screws 94 and set screw 96 until the screws 94 and 96 engage the margins of the raised ridge 90 and gutter 92 formed on the second elongate member 84. In this manner, the second elongate member 84 is affirmatively connected to the first elongate member 82, but the second elongate member is movable along its longitudinal axis relative to first elongate member 82. When the surgeon has placed the second elongate member 84 in the desired location, the set screw 96 is tightened in the gutter 92 to force the back side of second elongate member 84 against the inside of the "V" 98 of first elongate member 82 to retain the second elongate member 84 in that selected position relative to first elongate member 82 and prevent further sliding movement of second elongate member 84 along its longitudinal axis relative to first elongate member 82.

The mounting bracket 86 is then assembled to first elongate member 82 with the set screw 96 riding in the slot 88 of first elongate member 82 and another second elongate member 84 is inserted between the inside surface of the tabs 100 straddling the first elongate member 82 and the underside of the first elongate member 82. Guide screws 94 are then tightened sufficiently to retain the bracket and second elongate member 84 to first elongate member 82 and the second elongate member is slidably adjusted up and down first elongate member 82 to the desired location by the surgeon. Second elongate member 84 is slid back and forth along its longitudinal axis to the desired location relative to the patient's spinal column as described above and the guide and set screws 94, 96 are tightened to affirmatively retain the second elongate member 84 is the selected position relative to first elongate member 82 as described above. Washers of the appropriate shape and size are then selected as required to provide a connection between pedicle screw 34 (not shown) and the spinal stabilizer 80 which provides optimal load transfer between vertebrae and spinal stabilizer. A particular advantage of the embodiment shown in FIGS. 19–22 is its low "profile." In other words, when affixed to the vertebrae comprising a patient's spinal column, the dorsal extension of the embodiment shown in FIGS. 19–22 is minimized.

In the embodiment shown in FIGS. 23–26, the spinal stabilizer, indicated generally at reference numeral 102, is similar to the embodiment shown in FIGS. 14 and 15 above in that it is comprised of a first elongate member 104 which is formed in the shape of a rod (or rods as explained below) of the type marketed by MOSS® Miami as described in connection with FIGS. 14–15. However, in the embodiment shown in FIGS. 23–26, the second elongate member 106 is likewise configured in the shape of a rod. Threaded connectors 108 are provided which are identical in their function to that of the threaded connectors 68 of the embodiment shown in FIGS. 14–15, but the connectors 108 include an integral collar 109 in which the second elongate member 106 is journal so that member 106 is both sidably and rotatably attached to first elongate member 104. In this manner, after selecting the position of the second elongate member 106 along the length of the first elongate member 104, the second elongate member 106 is slid back and forth along its longitudinal axis 107 to the optimal position and then rotated relative to first elongate member 104 on its longitudinal axis 107 to a position which provides optimal load transfer through the connection between pedicle screw 34 (not shown) and the bearing surface 49 of washer 36 (likewise not shown). The set screw 111 in collar 109 is then tightened to retain the second member 106 in that position. Those skilled in the art who have the benefit of this disclosure will recognize that either of the embodiments shown in FIGS. 19–26 could function for their intended purpose with a single first elongate member running substantially parallel to the longitudinal axis of the patient's spine rather than two elongate members located lateral to the dorsal spines of the vertebrae.

It will also be recognized by those skilled in the art who have the benefit of this disclosure that any of the embodiments of the spinal stabilizer of the present invention may be utilized without cross-bars 32. In this additional embodiment, C-shaped clamps of a type known in the art including an aperture and means for engaging the washer constructed in accordance with the teachings of the present invention may be affixed to the pedicle screw 34 and positioned so as to clamp around the rod 22. A portion of a spinal stabilizer incorporating such clamps, shown at reference numeral 70, is shown in FIG. 31. In the embodiment shown in FIG. 31, the shoulder 50 of washer 36 extends downwardly through the aperture 52 in the C-clamp 70 and the concave surface 45 of washer 36 adjacent thereto engages the hemispherical surface 41 of the head 35 of pedicle screw 34, as does the bevel 53 on the underside of the aperture 52 of C-clamp 70. When the nut 38 is tightened onto the threads of pedicle screw 34, the angled bearing surface 49 of washer 36 provides effective load transfer from the pedicle screw 34 to the C-clamp 70 and, tightening C-clamp 70 around rod 22, to rod 22.

Although described in terms of the presently preferred embodiment shown in the figures, those skilled in the art will recognize from this description that changes can be made to the component parts of the present invention without changing the manner in which those component parts function to achieve their intended result. For instance, the present invention is equally adaptable to a spinal fixation system which is comprised of rods on either side of the processes of the vertebrae which may or may not be connected by a cross-bar or a system comprised of a single rod down the dorsal aspect of the spinal column after removal of the dorsal processes rather than the ladder-type system shown in the figures. All such changes, and the others known to those skilled in the art, are intended to fall within the scope of the following non-limiting claims.

What is claimed is:

1. A spinal stabilizer adapted for affixing to a vertebra of a patient with a pedicle screw comprising:

a first elongate member adapted for engaging a pedicle screw and having a slot formed therein;

a second elongate member;

a bolt extending through the slot in said first member and adapted for receiving a nut thereon for engaging said second member; and means formed on said bolt for retaining said bolt in the slot in said first member before said nut is engaged to said bolt.

2. The spinal stabilizer of claim 1 wherein said retaining means comprises an enlarged portion on said bolt for frictionally engaging the slot in said first member.

3. The spinal stabilizer of claim 1 wherein said bolt is slidably mounted in the slot in said first member.

4. The spinal stabilizer of claim 1 wherein said second member is rotationally movable relative to said first member along the longitudinal axis of said second member.

5. The spinal stabilizer of claim 1 wherein said bolt further comprises means for preventing rotation of said bolt relative to first elongate member as said nut is engaged thereto.

6. The spinal stabilizer of claim 1 wherein said second elongate member is attached to said first elongate member at approximately a 90° angle.

7. The spinal stabilizer of claim 1 wherein said second elongate member is slidably attached to said first elongate member for movement relative to said first elongate member.

8. The spinal stabilizer of claim 1 wherein said first elongate member is slidably attached to said second elongate member for movement relative to said second elongate member.

* * * * *